United States Patent [19]

Yanko et al.

[11] 4,028,410

[45] June 7, 1977

[54] PROCESS OF PREPARING 1,3-BIS(2-CHLOROETHYL)-1-NITROSOUREA

[75] Inventors: William H. Yanko, Centerville; Donald E. Sharp, Dayton, both of Ohio

[73] Assignee: The United States of America as represented by the Secretary of the Department of Health, Education and Welfare, Washington, D.C.

[22] Filed: Nov. 13, 1974

[21] Appl. No.: 523,334

[52] U.S. Cl. .............................. 260/553 R; 424/322
[51] Int. Cl.² ....................................... C07C 127/15
[58] Field of Search ............................... 260/553 R

[56] References Cited

UNITED STATES PATENTS 3,465,025    9/1969    Brownstein et al. ....... 260/553 R X

OTHER PUBLICATIONS

Johnston et al., *J. Med. Chem.*, vol. 18, No. 1, 1975, pp. 104–106.
Montero et al., *C. R. Acad. Sc. Paris*, t. 279, Series C, 1974, pp. 809–811.
Ryan et al., CA 17: 1792–1793 (1923).

*Primary Examiner*—Daniel E. Wyman
*Assistant Examiner*—Thomas A. Waltz
*Attorney, Agent, or Firm*—John S. Roberts, Jr.; Norman J. Latker; Thomas G. Ferris

[57] ABSTRACT

A method of producing 1,3-bis(2-chloroethyl)-1-nitrosourea (BCNU) by nitrosation of 1,3-bis(2-chloroethyl)-urea utilizing as a nitrosating agent dinitrogen trioxide ($N_2O_3$) in molar excess of theoretical wherein the molar excess of $N_2O_3$ ranges from 10–200% and preferably from 10–20%. The nitrosation reaction is conventionally carried out in the cold from 0° C to −20° C and a non-aqueous solvent is utilized. The preferred non-aqueous solvent is of the chlorinated variety; i.e., methylene dichloride. Other preferred solvents include related halogenated compounds such as ethylene dichloride, nitro-compounds such as nitromethane, acetonitrile, and simple ethers such as ethyl ether. Other less preferred but operable compounds include esters such as ethyl acetate, simple ketones such as acetones, and chloroform. Solvents to be avoided are olefins, unsaturated ethers and other unsaturated compounds, amines, malonate esters, acid anhydrides, and solvents which would interact with the reactant $N_2O_3$ and the urea as well as the product nitrosourea.

4 Claims, No Drawings

PROCESS OF PREPARING 1,3-BIS(2-CHLOROETHYL)-1-NITROSOUREA

The present invention relates to a process or method of producing 1,3-bis(2-chloroethyl)-1-nitrosourea which is also known as BCNU (NSC 409962). The product compound is an interesting one and has been utilized in cancer chemotherapy in recent years. The present process provides a method of preparation and recovery of BCNU which offers an increment of advantage as to yield and purity over known prior processes.

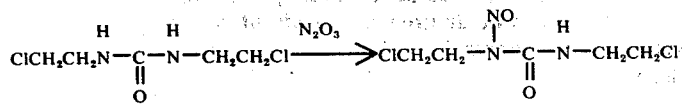

PRIOR ART

The patented prior art relating generally to the production of nitroso compounds is as follows.
U.S. Pat. No. 2,491,709 Briggs et al (ICI)
U.S. Pat. No. 2,683,696 Muller et al (Bayer)
U.S. Pat. No. 3,119,865 Weakley et al Additionally, previously known methods of producing BCNU utilizing aqueous formic acid and sodium nitrite or nitrous acid were compared and it was found that the yield of the present process or method was superior and also that the previous difficulty with side products and impurities was minimized by the present process. In addition, the present process is simpler and more easily conducted.

In the prior nitrosation using aqueous formic acid, the BCNU product forms as a low melting point solid which is difficult to handle. The yields from the aqueous process are about 60 percent. By comparsion in the present process utilizing $N_2O_3$, which is used anhydrous, the yield of crude is nearly quantitative and the product may be easily recrystallized.

THE STARTING MATERIALS

The Urea. This material is used in good grades, preferably CP, and the amount of urea utilized is the base on which the amounts of nitrosating agent are calculated. The starting material 1,3-bis(2-chloroethyl)urea is commercially available and also may be prepared readily from phosgene and ethyleneimine.

Dinitrogen trioxide ($N_2O_3$). Efficacy of reaction has been observed where this nitrosation agent was utilized in preference to the prior use of aqueous $NaNO_2$. It has also been found for stoichiometric reasons that an excess of the nitrosating agent ranging from 10–200% and preferably 10–20% based on urea is necessary to force the reaction to the right and obtain satisfactory completion. Furthermore, it is known from the literature art, Cotton, *Advanced Inorganic Chemistry*, Interscience, 1972, page 357, that this oxide exists in a pure state only at low temperatures and, therefore, reaction is conducted at nitrosation temperatures of about 0° C to −20° C.

The Solvent. In contrast to prior art methods, the present reaction is conducted in an organic milieu. The preferred non-aqueous solvent is of the chlorinated variety; i.e., methylene dichloride. Other preferred compounds include related halogenated compounds such as ethylene dichloride, nitro-compounds such as nitromethane, acetonitrile, and simple ethers such as ethyl ether. Other less preferred but operable compounds include esters such as ethyl acetate, simple ketones such as acetone, and chloroform. Solvents to be avoided are olefins, unsaturated ethers and other unsaturated compounds, amines, malonate esters, acid anhydrides, and solvents which would interact with the reactant $N_2O_3$ and the urea as well as the product nitrosourea. In general, the solvent should be low boiling (b.p. less than 120° C and preferably less than 100° C).

BCNU 1,3-bis(2-chloroethyl)-1-nitrosourea is one of a group of relatively recent drugs used against cancer and since 1972 has been charted by the National Cancer Institute for utilization against brain tumors, colon cancer, Hodgkins disease, lung cancer, and multiple myeloma. The modus of action of BCNU (NSC 409962) is as an alkylating agent. Such an alkylating agent is injurious to rapidly proliferating cells such as are present in many tumors and this action is known as antineoplastic activity.

EXAMPLE 1

1,3-Bis(2-chloroethyl)-1-nitrosourea

A suspension of 1.11 mmole (.205 g) of 1,3-bis(2-chloroethyl)urea in 8 ml methylene dichloride at −10° C was saturated with dinitrogen trioxide in 20% excess of theoretical. The heterogeneous mixture gradually changed to a green homogeneous solution. The methylene dichloride was evaporated, and the residue was extracted with 3 × 10 ml hexane. Evaporation of the hexane gave 0.1773 g of oil which was the crude BCNU (NSC 409962). The hexane insoluble portion, 0.0649 g, when treated with benzene, gave 0.020 g of 1,3-bis(2-chloroethyl)urea which was benzene insoluble. The benzene solubles were processed through a silica column (1 × 10 cm) and 0.0245 g of crude BCNU was obtained. The combined fractions of crude product amounted to 0.2018 g (85.1%)

In order to evaluate the product, the above crude was recrystallized from hexane to yield a first crop and from this first crop the ir spectrum was identical to that of known BCNU. A tlc (benzene on sillica) gave a single spot $R_f$ 0.35 (blue, 254 m$\mu$).

EXAMPLE 2

Comparative

A cold solution of 0.2346 g (3.4 mole) sodium nitrite in 2 ml water was slowly added to a stirred solution of 0.2727 g (1.47 mmole) 1,3-bis(2-chloroethyl)urea in 2 ml 88% formic acid at 0°. After 2 hours at 0°, 0.1449 g (46.0%) of an oil solid phase was removed. The ir spectrum of this fraction failed to agree with that of BCNU. After 2 days a small amount of crystalline BCNU slowly formed in this oil phase. A methylene dichloride extract of the aqueous phase yielded 0.0943 g (30.0%) of an amber oil whose ir spectrum agreed with that of a known sample of BCNU. Treatment of this oil with 5 ml hexane and cooling to 0° gave crystalline BCNU which formed an oil on warming to ambient temperature.

EXAMPLE 3

A cold slurry at −15° C of the 1,3-bis(2-chloroethyl)urea (2.0 mmole) in 8 ml methylene dichloride was treated with a small excess of $N_2O_3$. The 1,3-bis(2-chloroethyl)urea is almost insoluble in the cold methylene dichloride, whereas the BCNU product is quite soluble. Thus, treatment of the urea with the $N_2O_3$ changed the slurry to a homogeneous solution. Evaporation of the methylene dichloride gave a quantitative yield of crude BCNU. Purification by silica column chromatography gave 93.4% yield and recrystallization from benzene-heptane gave 85.2% yield of pure BCNU.

What is claimed is:

1. A method of producing 1,3-bis(2-chloroethyl)-1-nitrosourea which comprises reacting 1,3-bis(2-chloroethyl)-urea with an excess of dinitrogen trioxide in the cold at 0° C to −10° C in the presence of a solvent selected from at least one member of the group selected from methylene dichloride, nitromethane, ethylene dichloride, acetonitrile, and ethyl ether and free from solvents which would interact with the reactants dinitrogen trioxide, urea and the product compound nitrosourea.

2. The method according to claim 1 wherein the solvent is methylene dichloride.

3. The method according to claim 1 wherein the excess of dinitrogen trioxide utilized as a reactant is from about 10–200%.

4. The method according to claim 1 wherein the excess of dinitrogen trioxide utilized as a reactant is from about 10–20%.

* * * * *